United States Patent
Merk et al.

(10) Patent No.: US 10,182,834 B2
(45) Date of Patent: Jan. 22, 2019

(54) DELIVERY OF THROMBOLYTIC AGENT THROUGH ACTUATION MEMBER OF THROMBUS RETRIEVAL DEVICE

(71) Applicant: Cook Medical Technologies LLC, Bloomington, IN (US)

(72) Inventors: James C Merk, Terre Haute, IN (US); Dean R Puckett, Bloomington, IN (US); Darin J Voorhies, Bloomington, IN (US); Brent A Mayle, Spencer, IN (US); Keith R Milner, West Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 322 days.

(21) Appl. No.: 14/991,362

(22) Filed: Jan. 8, 2016

(65) Prior Publication Data
US 2016/0199080 A1    Jul. 14, 2016

Related U.S. Application Data

(60) Provisional application No. 62/101,300, filed on Jan. 8, 2015.

(51) Int. Cl.
*A61B 17/22* (2006.01)
*A61B 17/221* (2006.01)
*A61B 17/00* (2006.01)

(52) U.S. Cl.
CPC .. *A61B 17/221* (2013.01); *A61B 2017/00867* (2013.01); *A61B 2017/2212* (2013.01); *A61B 2017/22038* (2013.01); *A61B 2017/22039* (2013.01); *A61B 2017/22079* (2013.01); *A61B 2017/22084* (2013.01)

(58) Field of Classification Search
CPC ............ A61B 17/22; A61B 17/221; A61B 2017/2212; A61B 2017/22038; A61B 2017/32056; A61B 2017/2215; A61B 2017/22084
See application file for complete search history.

(56) References Cited

U.S. PATENT DOCUMENTS

| | | | |
|---|---|---|---|
| 3,996,938 | A | 12/1976 | Clark, III |
| 4,030,503 | A | 6/1977 | Clark, III |
| 5,336,178 | A | 8/1994 | Kaplan et al. |
| 5,972,019 | A | 10/1999 | Engelson et al. |
| 6,063,069 | A | 5/2000 | Cragg et al. |
| 6,096,053 | A | 8/2000 | Bates |
| 6,254,571 | B1 | 7/2001 | Hart |
| 6,325,815 | B1 | 12/2001 | Kusleika et al. |
| 6,454,775 | B1 | 9/2002 | Demarais et al. |

(Continued)

*Primary Examiner* — Victor Nguyen
(74) *Attorney, Agent, or Firm* — Brinks Gilson & Lione

(57) ABSTRACT

A method of treating a thrombus is provided wherein a device is advanced to the vicinity of the thrombus, a thrombolytic agent is applied to the thrombus, and an expandable basket of the device is expanded to capture at least a portion of the thrombus within the expandable basket. The device includes a catheter having a distal portion, a lumen and a plurality of openings on the outer surface of the catheter, through which the thrombolytic agent is supplied. The device further includes a sheath and may include a collar which assists in expanding the expandable basket as the sheath is moved relative to the catheter.

26 Claims, 4 Drawing Sheets

(56) References Cited

U.S. PATENT DOCUMENTS

| | | |
|---|---|---|
| 6,635,070 B2 | 10/2003 | Leeflang et al. |
| 6,749,619 B2 | 6/2004 | Ouriel et al. |
| 7,524,319 B2 | 4/2009 | Dubrul |
| 7,763,010 B2 | 7/2010 | Evans et al. |
| 7,875,050 B2 | 1/2011 | Samson et al. |
| 8,613,753 B2 | 12/2013 | Angel et al. |
| 2005/0021075 A1 | 1/2005 | Bonnette et al. |
| 2011/0106135 A1 | 5/2011 | Thompson et al. |
| 2011/0190797 A1 | 8/2011 | Fulkerson et al. |
| 2014/0371781 A1* | 12/2014 | Morgan ............... A61L 31/048 606/200 |

\* cited by examiner

DELIVERY OF THROMBOLYTIC AGENT THROUGH ACTUATION MEMBER OF THROMBUS RETRIEVAL DEVICE

CROSS REFERENCE

The present application is a continuation application of, and claims all benefit pursuant to 35 U.S.C. § 119(e) of U.S. Provisional Application Ser. No. 62/101,300, "Delivery of Thrombolytic Agent through Actuation Member of Thrombus Retrieval Device", filed Jan. 8, 2015, which is incorporated by reference in its entirety.

BACKGROUND

The field of the present disclosure relates to thrombus retrieval devices for use in thrombectomies and similar procedures.

Thrombus retrieval devices are frequently used in thrombectomies to dislodge and retrieve a thrombus or clot from narrow intraluminal passages. When a thrombus attaches or forms on the wall of an intraluminal passage, often thrombus retrieval devices are used to detach the thrombus from the wall of the intraluminal passage.

In some situations, the thrombus may have a hardened surface which prevents the device from capturing it, particularly if the device is required to pierce through a portion of the thrombus. Additionally, the thrombus may not detach easily from the wall of the intraluminal passage. In such a situation, a thrombolytic agent may be applied to the intraluminal passage. This may be applied generally intravenously, however general application of a thrombolytic agent reduces the ability of a patient's blood to clot properly and can cause severe problems in patients with high blood pressure or active bleeding. Furthermore, general application of a thrombolytic agent may require substantial time to affect a specific thrombus, sometimes requiring several hours of application.

To avoid the complications of general application of a thrombolytic agent, a catheter may be advanced to the location of the thrombus. Once present, the thrombolytic agent may be applied locally through the catheter, mitigating some of the effects of general application. However, the addition of the catheter adds a layer of complexity to the thrombectomy procedure, requiring either advancing a separate thrombolytic agent catheter over a wire guide separate from the retrieval device and its corresponding wire guide, or advancing and then retracting the thrombolytic agent catheter over the same wire guide used with the retrieval device. The former method of having separate wire guides for the thrombolytic agent catheter and the retrieval device can be difficult where the intraluminal passage is narrow, such as within the brain, where thrombectomies are often performed. The latter method of advancing the thrombolytic agent catheter over the same wire guide used with the retrieval device can be time consuming where the catheter may be advanced and then retracted before the retrieval device is advanced. Furthermore, this latter option can be even more time consuming where the initial application of the thrombolytic agent is found to be insufficient for the retrieval device to capture the thrombus. In such situations, the retrieval device may be retracted and the thrombolytic agent catheter advanced once again to apply the agent to the thrombus. This extremely time consuming operation is unacceptable where the thrombus is blocking blood flow to vital organs such as the heart or the brain, as is often the case.

What is needed is a method of efficiently applying a thrombolytic agent locally, while still being able to quickly capture and remove a thrombus from an intraluminal passage. It is further desirable that the thrombolytic agent may be capable of being applied while the retrieval device is attempting to capture the thrombus.

SUMMARY

Further areas of applicability will become apparent from the description provided herein. It should be understood that the description and specific examples are intended for the purpose of illustration only and are not intended to limit the scope of the present disclosure.

In one form of the present disclosure, a method of treating a thrombus is provided that includes advancing a device to the vicinity of the thrombus, where the device comprises a sheath having a lumen, a catheter disposed within the lumen, and an expandable basket arranged on the outer surface of the catheter. The catheter includes an agent lumen, a distal portion, and a plurality of openings arranged on an outer surface in communication with the agent lumen. A thrombolytic agent is applied to the thrombus through the plurality of openings on the outer surface of the catheter, and the catheter is moved relative to the sheath to expand the expandable basket and capture a portion of the thrombus within the expandable basket.

In another form of the present disclosure, A thrombus retrieval device is provided that includes a sheath having a lumen, a catheter disposed within the lumen, a collar encircling the catheter, and an expandable basket. The catheter includes an agent lumen, a distal portion, and a plurality of openings arranged on an outer surface of the catheter in fluid communication with the agent lumen. The expandable basket is arranged on the outer surface of the catheter, where a first end of the expandable basket is coupled to the collar and a second end is coupled to one of the sheath or the distal portion of the catheter. Relative movement between the sheath and the catheter acts to expand the expandable basket.

BRIEF DESCRIPTION OF SEVERAL VIEWS OF THE DRAWINGS

The disclosure may be more fully understood by reading the following description in conjunction with the drawings, in which.

The drawings described herein are for the purpose of illustration only and are not intended to limit the scope of the present disclosure in any way.

DETAILED DESCRIPTION

Figure 1:
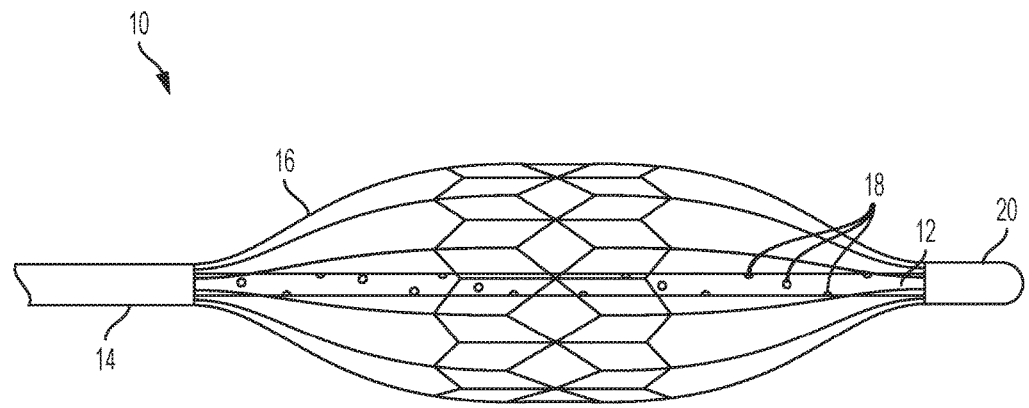
FIG. 1 is a side plan view of a first example of a thrombus retrieval device showing a sheath, a basket, and a catheter.

Referring now to the drawings, and particularly to FIG. 1, a thrombus retrieval device 10 includes a catheter 12, a sheath 14, and an expandable basket 16. The catheter 12 comprises a distal portion 20 and an agent lumen 36 (shown in FIGS. 6 and 7) through which a thrombolytic agent may be supplied, as well as a plurality of openings 18 arranged on the outer surface of the catheter 12, and in fluid communication with the agent lumen 36. The catheter 12 is arranged within a lumen of the sheath 14. The expandable basket 16 has a proximal end which is coupled to the sheath 14 and a distal end which is coupled to the distal portion 20 of the catheter 12.

The expandable basket 16 may be heatset in an elongated configuration such that, when no force is applied to the device 10, the expandable basket 16 will tend to remain radially unexpanded. Alternatively, the expandable basket 16 may be heatset in the expanded configuration such that, when a force is released, the expandable basket 16 radially expands. In either configuration, the expansion and/or contraction of the expandable basket 16 may be caused by relative movement between the catheter 12 and the sheath 14. For example, to expand the expandable basket 16, the catheter 12 may be partially retracted into the sheath 14. Alternatively, advancing the sheath 14 while the catheter 12 remains motionless would also result in expansion of the expandable basket 16.

When the expandable basket 16 is heatset in the elongated configuration, minimal force may be needed to maintain the device 10 in the elongated configuration while the expandable basket 16 is being advanced within the intraluminal passage 28. However, where the expandable basket 16 is heatset in the expanded configuration, the expandable basket 16 may be kept under a constant tension while advancing through the intraluminal passage 28 to prevent expansion of the expandable basket 16 and potential damage to the intraluminal passage 28. To prevent premature expansion of the expandable basket 16, an additional outer sheath (not shown) may be fitted over the expandable basket 16 while the expandable basket is being advanced through the intraluminal passage 28. Once the expandable basket 16 is advanced through or around the thrombus, the outer sheath may be retracted or the expandable basket 16 may be advanced beyond the distal end of the outer sheath, allowing expansion to occur. To allow for uniform expansion of the expandable basket 16, the basket 16 may be comprised of a shape memory alloy such as Nitinol. Alternatively, the basket 16 may comprise other alloys such as stainless steel or cobalt-chrome.

The catheter 12 shown in FIG. 1 is adapted to release a thrombolytic agent in the vicinity of a thrombus 30 (shown in FIGS. 4 and 5). Thrombolytic agent is supplied through the agent lumen 36 of the catheter 12 and is dispersed to the thrombus 30 through a plurality of openings 18 arranged on the outer surface of the catheter 12 which are in fluid communication with the agent lumen 36. The openings 18 can be arranged on the outer surface in a variety of patterns to achieve different effects. For example, the openings 18 shown in the embodiment of FIG. 1 are arranged circumferentially about the outer surface of the catheter 12 so that the thrombolytic agent is dispersed substantially around the entirety of the circumference of the catheter 12. This arrangement is ideal where the catheter 12 first penetrates the thrombus 30 before releasing the thrombolytic agent.

The distal end of the expandable basket 16 may be embedded within the distal portion 20 of the catheter 12. To accommodate the distal end of the expandable basket 16, the distal portion may be enlarged, as shown in FIG. 1, having a larger diameter than the rest of the catheter 12. The proximal end of the expandable basket 16 may be embedded within the wall of the sheath 14. If the basket is made of a material such as nitinol or stainless steel, the proximal end may be secured to the sheath 14 by welding the proximal end to a metal braid embedded within the wall of the sheath 14.

Figure 2:
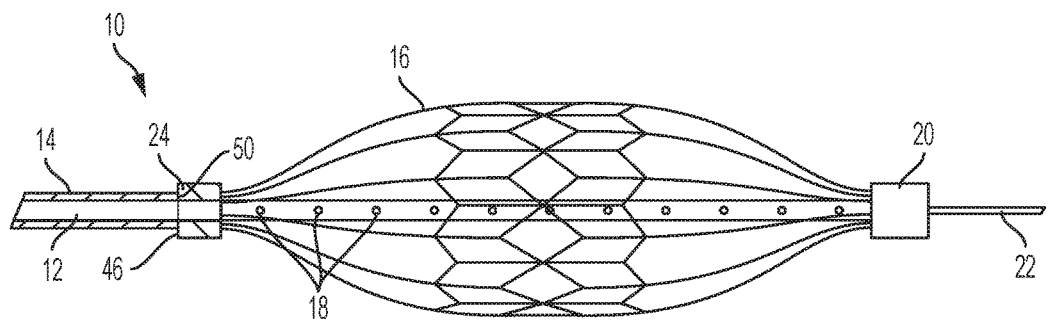
FIG. 2 is partial cross-sectional view of a second example of a thrombus retrieval device showing a catheter, a basket, a sheath, and a wire guide.

Referring to FIG. 2, another embodiment of a thrombus retrieval device 10 includes a catheter 12, an expandable basket 16, a proximal collar 24, and a wire guide 22. The catheter 12 encircles the wire guide 22 and may be advanced or retracted over the wire guide 22. The distal end of the expandable basket 16 is coupled to the distal portion 20 of the catheter 12, while the proximal end of the expandable basket 16 is coupled to the proximal collar 24. A sheath 14 may be advanced over the catheter 12 and pressed against a proximal surface 46 of the proximal collar 24 to cause the expandable basket 16 to expand. Alternatively, the sheath 14 may be advanced to the proximal surface 46 of the proximal collar 24, followed by retraction of the catheter 12 to cause radial expansion of the expandable basket 16. In order to expand the expandable basket 16, relative movement between the catheter 12 and the sheath 14 may occur to cause the proximal and distal ends of the expandable basket 16 to move closer to each other.

The proximal collar 24 is arranged to encircle the catheter 12 proximal of the distal portion 20 of the catheter 12. The proximal collar 24 may be coupled to the proximal end of the expandable basket 16 in a similar way as the distal end of the expandable basket 16 is coupled to the distal portion 20 of the catheter 12, such as being embedded within the proximal collar 24. Additionally, it may be desirable that the proximal collar 24 have an enlarged proximal surface 46 large enough to engage with the distal surface 50 of the sheath 14 when the sheath 14 is advanced against the proximal collar 24. The distal surface 50 of the sheath 14 and the proximal surface 46 of the proximal collar 24 may have a circumferential slot and groove arrangement with one surface having a groove and the other surface having a slot. In such an arrangement, when the surfaces 46, 50 engage, there will be less chance of slipping and more evenly applied force transmitted from the sheath 14 to the proximal collar 24.

Some embodiments of the device 10, such as the embodiment shown in FIG. 1, may not include a wire guide 22. In such embodiments, it may be desirable that the distal portion 20 of the catheter 12 have a rounded tip so that it may be advanced within the intraluminal passage 28 without damaging the intraluminal passage. Alternatively, the embodiment shown in FIG. 2 includes a wire guide 22 passing through the distal portion 20 of the catheter 12. In such an embodiment, at least one lumen must extend through the interior of the catheter 12 to an opening on the distal tip of the catheter 12, such that the catheter 12 may be advanced over a wire guide 22. Such a lumen may prevent or interfere with the rounding of the distal portion 20, however, advancing a catheter 12 over a wire guide 22 presents less risk to the intraluminal passage 28 than advancing the catheter 12 without a wire guide 22.

Alternatively, the distal portion 20 of the catheter 12 may have an elongated profile having variable stiffness such that the distal portion 20 has increasing stiffness from a flexible distal end to a stiffer proximal end. Additionally, the distal portion 20 may have a first diameter at the distal end and a larger second diameter at the proximal end. A distal portion 20 having such a configuration may be advantageous in approximating the shape and function of a wire guide 22, eliminating the need for a wire guide 22.

A plurality of openings 18 are arranged on the outer surface of the catheter 12 in fluid communication with the agent lumen 36 such that the thrombolytic agent may pass from the agent lumen 36 of the catheter 12 into the intraluminal passage 28. In the embodiment shown in FIG. 2, the openings 18 are arranged linearly on the outer surface of the catheter 12 so that the thrombolytic agent is dispersed around only a portion of the catheter 12 and in one general direction. Such a configuration may be beneficial where the catheter 12 is advanced around the thrombus 30 instead of through it so that the thrombolytic agent is dispersed as efficiently onto the thrombus 30 as possible.

Figure 3:
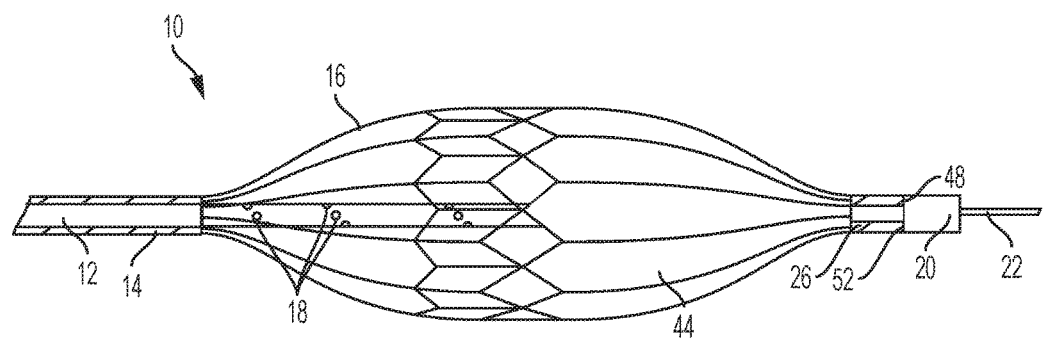
FIG. 3 is partial cross-sectional view of a third example of a thrombus retrieval device showing a catheter, a basket, a sheath, and a wire guide.

Referring to FIG. 3, another embodiment of a thrombus retrieval device 10 includes a sheath 14, an expandable basket 16, and a distal collar 26, all of which may be configured to be advanced over a catheter 12 having a plurality of openings 18 arranged on its outer surface. The catheter 12 has a distal portion 20 which has a larger diameter than the main body of the catheter. This larger diameter on the distal portion 20 also provides a proximal surface 52. The device 10 is advanced over the catheter 12 until a distal surface 48 of the distal collar 26 engages with the proximal surface 52 of the distal portion 20. After the distal collar 26 has engaged the distal portion 20 of the catheter 12, relative movement between the catheter 12 and the device 10 causes the expandable basket 16 to expand radially. Such relative motion brings the distal end and proximal end of the expandable basket 16 closer together.

The expandable basket 16 may also include a covering 44 coupled to the outer surface of at least a portion of the expandable basket 16. This covering 44 may be arranged on the distal portion of the expandable basket and expands radially as the expandable basket 16 expands. As a result, the portion of the covering 44 nearer to the distal collar 26 may not expand at all, while the portion of the covering 44 nearer to the middle of the expandable basket 16 may expand more as the expandable basket 16 is expanded. The covering 44 may be arranged on the inside or the outside of the expandable basket 16 and may be useful in dislodging and transporting the thrombus 30. For example, once the thrombus 30 is captured within the expandable basket 16, the covering 44 arranged on the distal portion of the basket 16 may be useful in moving the thrombus 30 by retracting the expandable basket 16 by defining the distal-most point at which the thrombus 30 may be within the intraluminal passage 28 while retracting the expandable basket 16. Alternatively, the covering 44 arranged on a proximal portion of the expandable basket 16 may be useful in moving the thrombus 30 while advancing the expandable basket 16.

Each embodiment shown in FIGS. 1-3, as well as other similar embodiments, is configured to be utilized within an intraluminal passage 28 having a diameter between about 4 mm and 24 mm. The diameter of the intraluminal passage 28 may vary by its location within the circulatory system as well as its function as either a vein or an artery. Furthermore, in at least some situations, it may be desirable for the device 10, in a compressed state, to be able to fit within an introducer sheath having a no larger than a 5 Fr (1.67 mm) diameter opening, however, some embodiments of the device 10 may be used with an introducer with a diameter as large as 12 Fr (4.00 mm).

Figure 4A:
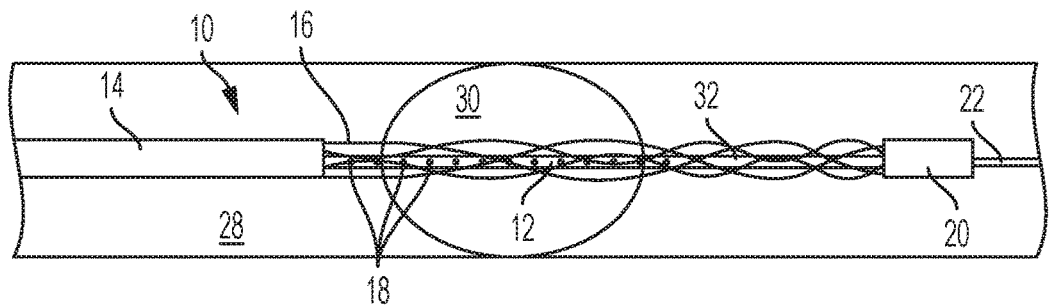
FIGS. 4A and 4B are partial cross-sectional views of a fourth example of a thrombus retrieval device within an intraluminal passage showing a thrombus and a thrombus retrieval device.
Figure 4B:
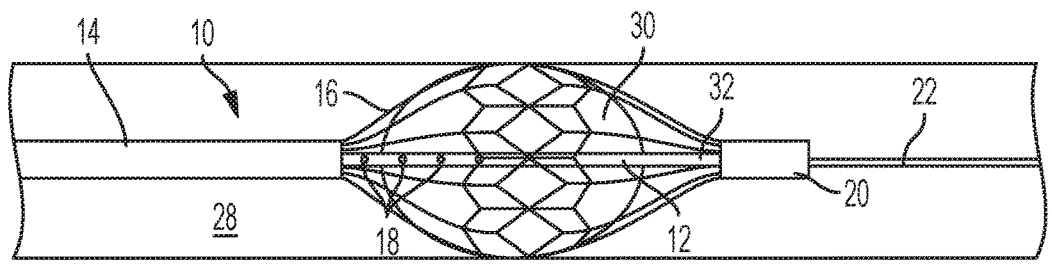

Referring to FIGS. 4A and 4B, a method of using a thrombus retrieval device 10 is shown. FIG. 4A shows a thrombus 30 occluding an intraluminal passage 28. Initially, a wire guide 22 is advanced through the intraluminal passage 28. If the thrombus 30 is sufficiently pliable, the wire guide 22 will pass through the thrombus 30. After the distal end of the wire guide 22 has been advanced beyond the thrombus 30, the device 10 shown in FIG. 4A is advanced over the wire guide 22 and through the thrombus 30. Once the device 10 is positioned passing through at least a portion of the thrombus 30, a thrombolytic agent can be released through the openings 18 in the catheter 12 to be applied to the thrombus 30. This application of the thrombolytic agent softens portions of the thrombus 30 and may make it easier to dislodge the thrombus 30 from the walls of the intraluminal passage 28. As shown in FIG. 4B, the catheter 12 is then retracted to cause the expandable basket 16 to expand and capture at least a portion of the thrombus 30 within the basket 16. The device 10 can then be retracted to dislodge the thrombus 30 from the walls of the intraluminal passage 28 and removed from the intraluminal passage.

It may be desirable that the openings 18 on the outer surface of the catheter 12 are positioned only in the area around where the catheter 12 passes through the thrombus 30. In this manner, the release of the thrombolytic agent may be focused only to the intended area of effect, reducing the total amount of thrombolytic agent which may need to be used. As shown in FIGS. 4A and 4B, where the catheter 12 retracts to expand the expandable basket 16, there may be a sealed portion 32 of the catheter separating the distal portion 20 and the openings 18. This sealed portion 32 will not allow the thrombolytic agent to pass through to the outer surface and should be at least as long as the retraction distance of the catheter 12 when expanding the expandable basket 16, but may be longer or shorter. When the expandable basket 16 is expanded, the sealed portion 32 may retract into the thrombus and displace the portion of the catheter 12 having the openings 18 and making application of the thrombolytic agent more difficult during the process of expansion of the expandable basket 16.

Figure 5A:
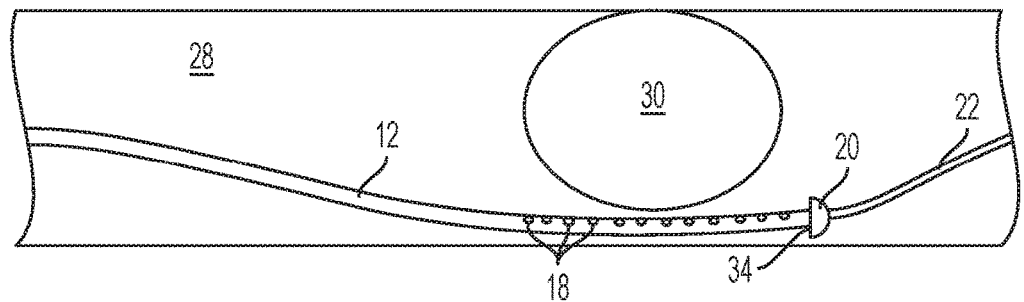
FIGS. 5A-5C are partial cross-sectional views of a fifth example of a thrombus retrieval device within an intraluminal passage showing a thrombus and a thrombus retrieval device.
Figure 5B:
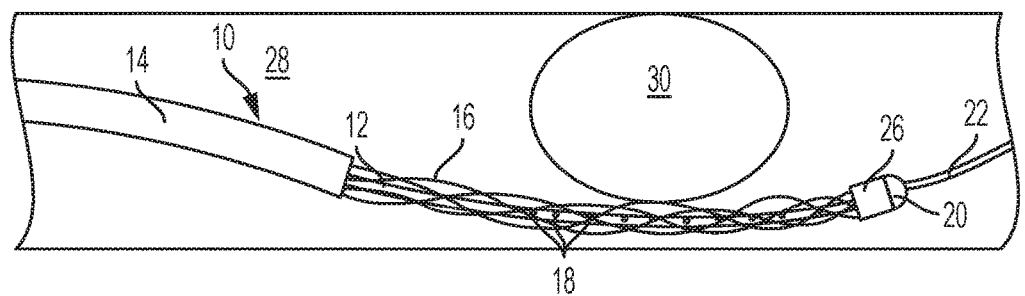
Figure 5C:
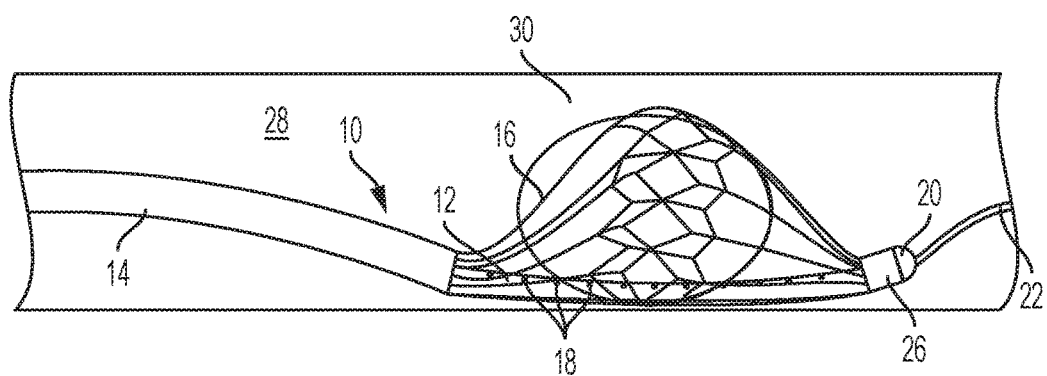

Referring to FIGS. 5A-5C, an alternative method of using a thrombus retrieval device 10 is shown. In some instances, it may be difficult to advance the catheter 12 through the thrombus 30 before application of the thrombolytic agent. This may be because the thrombus 30 is either too hardened or too brittle. In such situations, the wire guide 22 may be advanced around the thrombus 30 on one sides of the intraluminal passage 28. A catheter 12 may be advanced over the wire guide 22 and be aligned so that openings 18 in the catheter 12 overlap with at least a portion of the thrombus 30. The thrombolytic agent may then be applied to soften or dissolve the thrombus 30. Alternatively, an introducer sheath (not shown) may be advanced to the vicinity of the thrombus 30 before the device 10 is advanced. The device 10 may then be advanced to capture and remove the thrombus 30. The introducer sheath should be sufficiently large to contain the device 10 while the expandable basket 16 is in the elongated configuration. Advancing the device through the introducer sheath may ease the advancement of the device to the thrombus 30 and may prevent the elongated basket 16 from contacting the wall of the intraluminal passage 28 while being advanced. An aspiration catheter may also be advanced within the introducer sheath, or may be advanced separately.

Once the thrombus 30 has been treated by the thrombolytic agent, the thrombus retrieval device 10 may be advanced over the catheter 12 and the expandable basket 16 may be expanded to capture at least a portion of the thrombus 30. In the embodiment shown in FIGS. 5A-5C, a thrombus retrieval device 10 is shown similar to the embodiment shown in FIG. 3, having an expandable basket 16 coupled to a sheath and a distal collar 26. However, other embodiments of the thrombus retrieval device 10 may be used instead to the same effect. The further distal movement of the retrieval device 10 is stopped and prevented by a catch 34 arranged on a proximal side of the distal portion 20 of the catheter 12. The catch 34 may take the form of a proximally facing engaging surface, or any other protrusion which extends outwardly from the body of the catheter 12.

In the embodiment shown in FIG. 5C, when the distal collar 26 is advanced against the distal portion 20 of the catheter 12, the expandable basket 16 begins to expand from one side of the thrombus 30. Depending on the design of the basket 16, expansion may occur on one side to pass through and capture the thrombus 30. This one sided expansion may put additional force on the distal collar 26, sheath 14, and catheter 12, pressing these components away from the walls of the intraluminal passage 28 and towards the thrombus 30 and the center of the intraluminal passage 28. If, during the expansion of the expandable basket 16, the wires of the expandable basket 16 are unable to pass through or around the thrombus 30, additional thrombolytic agent may be applied from the openings 18 in the catheter 12. This is particularly useful where the openings 18 of the catheter 12 remain stationary as the expandable basket 16 is being expanded, as shown in FIG. 5C. Once at least a portion of the thrombus 30 has been captured, the expandable basket 16 may be retracted to be removed from the intraluminal passage 28. Alternatively, the aspirator catheter (not shown) may be advanced to the point of retrieval to remove the thrombus 30. Alternatively, the aspiration catheter may be positioned in the vicinity of an introducer (not shown) into the intraluminal passage and the device may be retracted so as to bring the thrombus to the aspiration catheter. This may be the case where the aspiration catheter is too large to be advanced further into the intraluminal passage. In such cases, the expandable basket 16 may be retracted to bring the thrombus 30 to the opening of the aspiration catheter for removal from the intraluminal passage.

The expandable basket 16 of the device 10 shown in FIGS. 5A-5C may require wires with greater strength than other embodiments of the device 10 to prevent the expandable basket 16 from collapsing while moving to the expanded configuration. The additional strength may be provided by utilizing wires having a greater thickness than wires used in other embodiments of the expandable basket 16. Alternatively, a stronger material than Nitinol may be used for the wires of the expandable basket 16, such as stainless steel or another comparable metal alloy.

An expandable funnel (not shown) may be used alongside the device 10. Depending on the flow of fluid within the intraluminal passage 28, a funnel may be positioned and expanded either distally or proximally of the thrombus 30 to prevent portions of the thrombus 30 from breaking off and escaping further into the intraluminal passage 28. The funnel may be advanced within the intraluminal passage 28 by a separate catheter, or may be advanced through a lumen of the device 10.

The addition of a funnel is particularly useful where the expandable basket 16 is meant to capture only a portion of the thrombus 30 at one time. The funnel can be positioned to prevent the thrombus 30 from moving within the intraluminal passage, while the expandable basket 16 is advanced and retracted, extracting smaller portions of the thrombus 30 at a time.

A wire guide 22 may be incorporated into catheter 12 in at least three designs. A first design incorporates the wire guide 22 within the agent lumen 36 without a separate lumen exclusively for the wire guide 22. This design is simple to construct and operate, but has the disadvantage of leaking thrombolytic agent from the distal portion 20 of the catheter, where the wire guide 22 extends beyond the catheter 12. The leaking of the thrombolytic agent can be minimized by further including a ring projecting inwardly from the wall of an inner surface of the catheter 12 and into the agent lumen 36 at or near the distal portion 20 of the catheter 12. The wire guide 22 passes through this ring, minimizing a gap in the opening of the agent lumen 36 at least partially filled by the wire guide 22. If the gap is sufficiently small, the openings 18 to the outer surface of the catheter 12 will become the primary outlet for the thrombolytic agent. Thus, there is an annular space around the wire guide 22 within the agent lumen 36 to allow the thromobolytic agent to flow to the openings 18 but the annular space is at least partially enclosed at the end by the inwardly extending ring.

Figure 6:
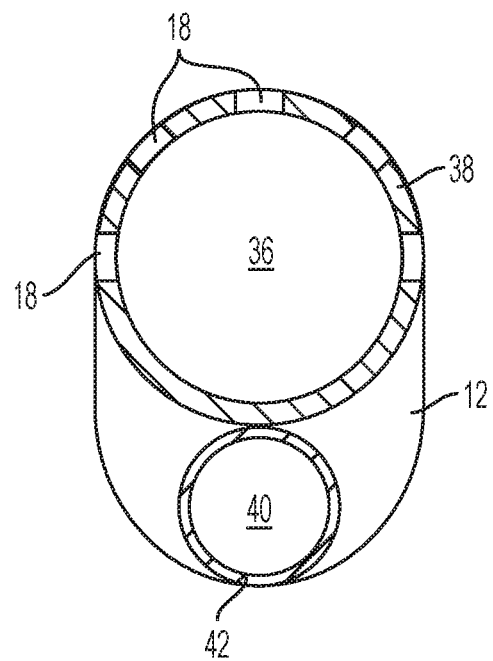
FIG. 6 is a cross-sectional view of a catheter showing a fluid lumen and a wire guide lumen.

Alternatively, referring to FIG. 6, a second design is shown including a wire guide lumen 40 in a wire guide lumen liner 42 and an agent lumen 36 in a agent lumen liner 38, where each lumen is separate from one other and contained within the catheter 12 body. This configuration is ideal where the openings 18 from the agent lumen 36 to the outer surface are arranged around only a portion of the circumference of the catheter, as the wire guide lumen 40 will necessarily block at least some of the circumference of the catheter 12.

Figure 7:
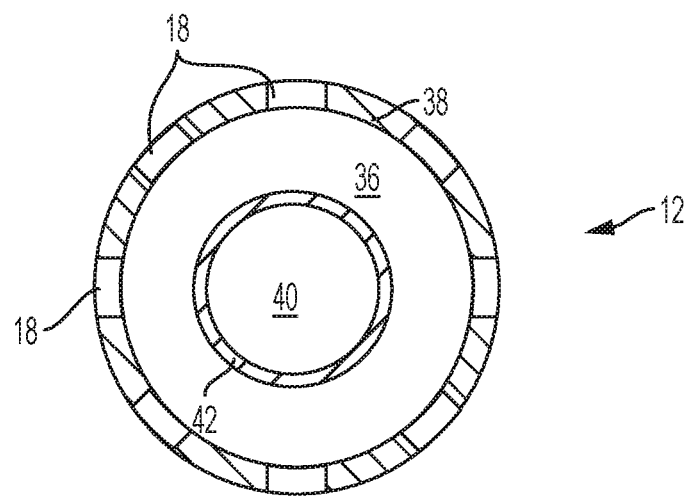
FIG. 7 is a cross-sectional view of another catheter showing a fluid lumen and a wire guide lumen.

Referring to FIG. 7, a third design is shown including a wire guide lumen 40 within a wire guide lumen liner 42 which is contained within an agent lumen 36. In such a configuration, the openings 18 may pass through the agent lumen liner 38 to allow fluid flow from the agent lumen 36 to the outer surface of the entire circumference of the catheter 12. Although such an arrangement allows thrombolytic agent to be dispersed around the entire circumference of the catheter 12, it may also require a larger diameter catheter 12 to achieve comparable agent flow as the previous designs, as the wire guide lumen 40, in this embodiment, fills a portion of the agent lumen's 36 cross-sectional area. The agent lumen 36 is enclosed at the end with a tip that connects the liners 42, 38.

Accordingly, it is now apparent that there are many advantages provided herein. In addition to the advantages that have been described, it is also possible that there are still other advantages that are not currently recognized but which may become apparent at a later time.

While preferred embodiments have been described, it should be understood that the invention is not so limited, and modifications may be made without departing from the invention. The scope of the invention is defined by the appended claims, and all devices that come within the meaning of the claims, either literally or by equivalence, are intended to embrace them.

We claim:
1. A method of treating a thrombus, comprising:
    advancing a device to the vicinity of the thrombus, wherein the device comprises a sheath having a lumen, a catheter disposed within the lumen, the catheter having an agent lumen, a distal portion, and a plurality of openings in fluid communication with the agent lumen, the openings being arranged on an outer surface of the catheter, and an expandable basket arranged on the outer surface of the catheter;

supplying a thrombolytic agent to the agent lumen and applying the thrombolytic agent to the thrombus through the plurality of openings on the outer surface of the catheter;

positioning the basket alongside the thrombus; and moving the catheter relative to the sheath to expand the expandable basket from the collapsed position after positioning the basket alongside the thrombus and capture at least a portion of the thrombus within the expandable basket.

2. The method of claim 1, wherein the expandable basket further comprises a covering coupled to a distal portion of the expandable basket.

3. The method of claim 1, further comprising retracting the device with the portion of the thrombus captured in the expandable basket while maintaining a relative position of the device with respect to the catheter, such that the expandable basket remains in an expanded configuration.

4. The method of claim 3, further comprising, retracting the device such that the portion of the thrombus is in the vicinity of an aspiration catheter, and moving the device relative to the catheter to radially contract the expandable basket and release the portion of the thrombus.

5. The method of claim 1, wherein the device is advanced through a portion of the thrombus so that at least one of the plurality of openings is positioned inside the thrombus.

6. The method of claim 5, wherein the plurality of openings are arranged circumferentially about the outer surface of the catheter so that the thrombolytic agent is dispersed substantially around an entire circumference of the catheter.

7. The method of claim 1, wherein the device is advanced distally beyond the portion of the thrombus such that at least one of the openings is aligned with the thrombus.

8. The method of claim 7, wherein the plurality of openings are arranged linearly on the catheter such that the thrombolytic agent is dispersed around only a portion of the circumference of the catheter.

9. The method of claim 1, wherein the expandable basket further comprises a covering coupled to a proximal portion of the expandable basket.

10. The method of claim 1, wherein the catheter further comprises a wire guide which passes through the agent lumen.

11. The method of claim 10, wherein the catheter further comprises a ring projecting inwardly from a wall of the agent lumen at or near the distal portion of the catheter, configured to receive the wire guide.

12. The method of claim 1, wherein the catheter further comprises a wire guide within a wire guide lumen, wherein the wire guide lumen is outside of the agent lumen.

13. The method of claim 1, wherein a proximal end of the expandable basket is coupled to the sheath and a distal end of the expandable basket is coupled to the distal portion of the catheter.

14. The method of claim 1, further comprising a collar encircling a portion of the catheter and having a proximal surface, wherein a proximal end of the expandable basket is coupled to the collar, and a distal end of the expandable basket is coupled to the distal portion of the catheter.

15. The method of claim 14, further comprising advancing the sheath over the catheter after the catheter, collar, and expandable basket have been advanced, wherein the sheath is advanced to engage with the proximal surface of the collar.

16. The method of claim 14, wherein the thrombolytic agent is applied while the expandable basket is being expanded.

17. The method of claim 1, further comprising a collar encircling a portion of the catheter and having a distal surface, wherein a proximal end of the expandable basket is coupled to the sheath, and a distal end of the expandable basket is coupled to the collar.

18. The method of claim 17, further comprising advancing the catheter in the vicinity of the thrombus before the sheath, collar, and expandable basket have been advanced, wherein the distal surface of the collar is configured to engage with a proximal surface of the distal portion of the catheter.

19. The method of claim 17, wherein the expandable basket is heatset in an elongated configuration so that the expandable basket will expand only when compressed by relative movement between the sheath and the collar.

20. The method of claim 1, wherein expansion of the expandable basket and capture of the portion of the thrombus occur simultaneously.

21. A method of treating a thrombus, comprising:

advancing a device to the vicinity of the thrombus, wherein the device comprises a sheath having a lumen, a catheter disposed within the lumen, the catheter having an agent lumen, a distal portion, and a plurality of openings in fluid communication with the agent lumen, the openings being arranged on an outer surface of the catheter, and an expandable basket arranged on the outer surface of the catheter, the expandable basket comprising a plurality of wires;

supplying a thrombolytic agent to the agent lumen and applying the thrombolytic agent to the thrombus through the plurality of openings on the outer surface of the catheter;

positioning the basket alongside the thrombus; and expanding the expandable basket from the collapsed position after positioning the basket alongside the thrombus, such that at least a portion of the plurality of wires pass through the thrombus.

22. The method of claim 21, wherein the device is advanced around the thrombus.

23. The method of claim 21, wherein the device is advanced through the thrombus.

24. The method of claim 21, further comprising applying additional thrombolytic agent to the thrombus wherein the wires of the expandable basket cannot pass through the thrombus.

25. The method of claim 21, further comprising dispersing the thrombolytic agent around the entire circumference of the catheter.

26. The method of claim 21, further comprising focusing the dispersion of the thrombolytic agent to a portion of the circumference of the catheter which faces the thrombus.

* * * * *